(12) United States Patent
Wang et al.

(10) Patent No.: US 10,883,091 B2
(45) Date of Patent: Jan. 5, 2021

(54) DNA POLYMERASE VARIANT AND APPLICATION THEREOF

(71) Applicant: MGI TECH CO., LTD., Shenzhen (CN)

(72) Inventors: Lin Wang, Shenzhen (CN); Fen Liu, Shenzhen (CN); Yuliang Dong, Shenzhen (CN); Wenwei Zhang, Shenzhen (CN); Chongjun Xu, Shenzhen (CN); Snezana Drmanac, Shenzhen (CN)

(73) Assignee: MGI TECH CO., LTD., Shenzhen (CN)

(*) Notice: Subject to any disclaimer, the term of this patent is extended or adjusted under 35 U.S.C. 154(b) by 0 days.

(21) Appl. No.: 16/505,121

(22) Filed: Jul. 8, 2019

(65) Prior Publication Data
US 2019/0330602 A1 Oct. 31, 2019

Related U.S. Application Data

(63) Continuation-in-part of application No. PCT/CN2017/070609, filed on Jan. 9, 2017.

(51) Int. Cl.
*C12N 9/12* (2006.01)
*C12Q 1/6869* (2018.01)

(52) U.S. Cl.
CPC ......... *C12N 9/1252* (2013.01); *C12Q 1/6869* (2013.01); *C12Y 207/07007* (2013.01); *C07K 2319/20* (2013.01); *C07K 2319/21* (2013.01); *C07K 2319/22* (2013.01); *C07K 2319/41* (2013.01); *C07K 2319/43* (2013.01)

(58) Field of Classification Search
None
See application file for complete search history.

(56) References Cited

FOREIGN PATENT DOCUMENTS

| CN | 104854237 A | 8/2015 |
|---|---|---|
| WO | 2009131919 A2 | 10/2009 |
| WO | 2015200693 A1 | 12/2015 |
| WO | 2016054096 A1 | 4/2016 |

OTHER PUBLICATIONS

He, Shaozong et al., Study on modification of Taq DNA polymerase with cationic peptide of human lactoferrin, Journal of Sichuan University (Natural Science Edition), May 28, 2016, 633-638, 53(3), with English Abstract.
Hashimoto, H et al., Crystal Structure of DNA Polymerase frim Hyperthermophilie Archaeon Pyrococcus Kodakaraensis KOD1, Journal of Molecular Biology, Feb. 23, 2001, 469-477, 306(3).
International Search and Written Opinion for PCT Application No. PCT/CN2017/070609, dated Oct. 17, 2017.
Office Action issued for European patent application serial No. EP 17889883.9 dated Jun. 2, 2020.

*Primary Examiner* — Anand U Desai
(74) *Attorney, Agent, or Firm* — Westman, Champlin & Koehler, P.A.; Z. Peter Sawicki; Amanda M. Prose

(57) ABSTRACT

Disclosed in the present disclosure is a recombinant DNA polymerase. The recombinant DNA polymerase is any one selected from: A) a protein, having amino acid modifications at positions 408, 409 and 485, and at least one of amino acid modification(s) at positions 53, 59, 199, 243, 526, 558, 613, 641, 671, 673, 674, 692 and 709 compared to the amino acid sequence of a wild-type KOD DNA polymerase; B) a protein derived from the protein in A), formed by deleting amino acids 1 to 29 from a C-terminus of the protein in A) and keeping the remaining amino acids unchanged; and C) a protein derived from the protein in A) or B), formed by connecting a tag to the N-terminus or C-terminus of the amino acid sequence of the protein in A) or B), wherein the protein in A), B) and C) has DNA polymerase activity.

12 Claims, 3 Drawing Sheets
Specification includes a Sequence Listing.

DNA POLYMERASE VARIANT AND APPLICATION THEREOF

CROSS-REFERENCE TO RELATED APPLICATIONS

This application is a U.S. continuation-in-part application based upon PCT Application No. PCT/CN2017/070609, filed with the China National Intellectual Property Administration on Jan. 9, 2017, and published as WO 2018/126470 on Jul. 12, 2018, the entire content of which is incorporated herein by reference.

FIELD

The present disclosure relates to the field of biotechnology, particularly to a recombinant DNA polymerase.

BACKGROUND

DNA polymerase catalyzes the rapid and accurate replication of DNA in chromosomes of a living organism, which plays an important role in maintaining the stability of genetic materials in the living organism. The *Escherichia coli* (*E. coli*) based polymerases, mainly including polymerases I, II and III, are respectively divided into three families A, B and C due to their difference in amino acid sequences. Despite their similar nucleotide binding sites in structure, the polymerases exhibit different recognition mechanisms for a nucleotide and its analogues because they have significant different motifs. The polymerase which is tightly associated with the activity in a living organism, is thus in a core position for molecular biology technologies, especially in the aspects of molecular cloning, PCR reaction, site-directed mutation and DNA sequencing. For the molecular biology technologies, DNA polymerase is critical for the recognition of a nucleotide and its analogues or the binding of the nucleotide to a template.

Many practical applications rely on the DNA polymerase which is capable of accurately recognizing the nucleotide or its analogs added. For example, for the sequencing-by-synthesis (SBS) with high throughput and low price compared to other current sequencing methods, the nucleotide which is labeled with fluorescein benefits the identification of the bases of a DNA template, thereby obtaining the base sequences of the DNA template. During the SBS method, the addition of DNA polymerase recognizing an artificially modified nucleotide or its nucleotide analogs (such as a reversible terminator with a fluorescent label) is critical. In current DNA polymerization reaction, the DNA polymerase in the prior art which cannot polymerize the artificially modified nucleotide or its nucleotide analogs effectively has limited the replication of DNA. Thus, it is important to increase the polymerization efficiency of DNA polymerase to polymerize the artificially modified nucleotide or its nucleotide analogs, especially for the sequencing method.

SUMMARY

Embodiments of the present disclosure seek to solve at least one of the problems existing in the related art to at least some extent.

For this purpose, in one aspect, the present disclosure in embodiments provides a DNA polymerase variant, including amino acid mutations at positions 408, 409 and 485 compared to the amino acid sequence of a wild-type KOD DNA polymerase depicted in SEQ ID NO:1, wherein the DNA polymerase variant has DNA polymerase activity.

In some embodiments, the amino acid mutation includes substitution of leucine at position 408 with isoleucine, tyrosine, proline, valine, cysteine, serine, alanine or methionine; substitution of tyrosine at position 409 with alanine or glycine; and substitution of alanine at position 485 with histidine, asparagine, lysine, aspartic acid or glutamic acid.

In some embodiments, the DNA polymerase variant further includes at least one of amino acid mutations at positions 53, 59, 199, 243, 526, 558, 613, 641, 671, 673, 674, 692 and 709 compared to the amino acid sequence of the wild-type KOD DNA polymerase.

In some embodiments, the at least one of amino acid mutations at positions 53, 59, 199, 243, 526, 558, 613, 641, 671, 673, 674, 692 and 709 is selected from the group consisting of:
substitution of lysine at position 53 with methionine;
substitution of histidine at position 59 with phenylalanine;
substitution of lysine at position 199 with methionine;
substitution of arginine at position 243 with methionine;
substitution of lysine at position 526 with methionine;
substitution of lysine at position 558 with methionine;
substitution of arginine at position 613 with methionine;
substitution of arginine at position 641 with methionine;
substitution of lysine at position 671 with methionine;
substitution of tyrosine at position 673 with phenylalanine;
substitution of lysine at position 674 with alanine;
substitution of lysine at position 692 with methionine; and
substitution of arginine at position 709 with methionine.

In some embodiments, the DNA polymerase variant is further modified by deleting amino acids 1 to 29 from the C-terminus of the DNA polymerase variant.

In some embodiments, the DNA polymerase variant is further labeled at the N-terminus or C-terminus with a tag.

In some embodiments, the tag is selected from Poly-Arg, Poly-His, FLAG, Strep-tag II and c-myc.

In some embodiments, the DNA polymerase variant consists of the amino acid sequence of SEQ ID NO: 8, SEQ ID NO: 10 and SEQ ID NO: 12.

In another aspect, provided in embodiments is a nucleic acid encoding the DNA polymerase variant as described above.

In a further aspect, provided in embodiments is a method for sequencing, where the method is conducted under the DNA polymerase variant as described above.

BRIEF DESCRIPTION OF THE DRAWINGS

The above and/or additional aspects and advantages of the present disclosure will become apparent and easily understood from the description of embodiments in combination with the accompanying drawings, in which.

DETAILED DESCRIPTION

Figure 1:
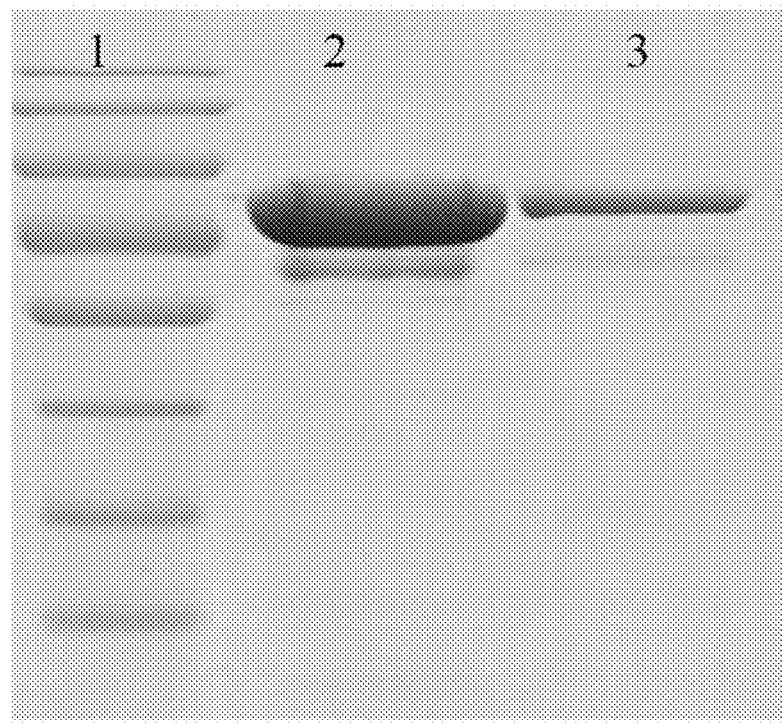
FIG. 1 is a schematic graph showing the electrophoresis result of purification detection of purified wild-type KOD DNA polymerase according to one embodiment of the present disclosure.

The present disclosure is described in detail with reference to the drawings and specific embodiments, where the same or similar elements and the elements having same or similar functions are denoted by like reference numerals throughout the descriptions. The embodiments described herein with reference to drawings are explanatory and used to generally understand the present disclosure. The embodiments shall not be construed to limit the present disclosure.

The terms "a," "an," "the" and similar referents used in the context of describing the invention (especially in the context of the following claims) are to be construed to cover both the singular and the plural, unless otherwise indicated herein or clearly contradicted by context. The use of any and all examples, or exemplary language (e.g., "such as") described herein is intended merely to better illuminate the invention and does not pose a limitation on the scope of the invention otherwise claimed. No language in the specification should be construed as indicating any non-claimed element essential to the practice of the invention.

Terms such as "first" and "second" are used herein for purposes of description and are not intended to indicate or imply relative importance or significance, impliedly indicate the quantity of the technical feature referred to or indicate the ordinal relation of elements or technical features. Thus, the feature defined with "first" and "second" may comprise one or more this feature. In the description of the present disclosure, "a plurality of" means two or more than two this features, unless specified otherwise.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of". The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Protein: A protein typically comprises one or more peptides or polypeptides. A protein is typically folded into a 3-dimensional form, which may be required for the protein to exert its biological function. The sequence of a protein or peptide is typically understood to be the order, i.e. the succession of its amino acids.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. For example, an expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA polymerase promoter sequence. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

The experimental methods used in the following examples are conventional methods unless otherwise specified.

The materials, reagents and the like used in the following examples are commercially available unless otherwise specified.

The present disclosure is accomplished by present inventors based on the following discoveries: a series of variants of KOD DNA polymerase with improved catalytic and physicochemical properties are generated, by mutating amino acids in some sites of the wide-type KOD DNA polymerase through semi-rational design, enzyme variant library construction and high-throughput screening, based on dynamic simulation of three-dimensional structures of naturally occurring DNA polymerases and their artificially modified variants and statistical inference of sequence information of the DNA polymerases. Such the variants obtained are poor at adsorbing on the surface of a chip and are easily eluted from the surface of the chip, thereby being suitable for DNA sequencing in a sequencing chip.

In some embodiments, the protein provided in the present disclosure is any one selected from A) a protein, having amino acid modifications at positions 408, 409 and 485, and at least one of amino acid modification(s) at positions 53, 59, 199, 243, 526, 558, 613, 641, 671, 673, 674, 692 and 709 compared to the amino acid sequence of a wild-type KOD DNA polymerase;

B) a protein derived from the protein in A), formed by deleting amino acids 1 to 29 from a C-terminus of the protein in A) and keeping the remaining amino acids unchanged; and C) a protein derived from the protein in A) or B), formed by connecting a tag to an N-terminus or C-terminus of the amino acid sequence of the protein in A) or B), where the protein in A), B) and C) each has DNA polymerase activity.

In some embodiments, the protein in A) has amino acid modifications at positions 408, 409 and 485, and at least two of amino acid modifications at positions 53, 59, 199, 243, 526, 558, 613, 641, 671, 673, 674, 692 and 709 compared to the amino acid sequence of the wild-type KOD DNA polymerase, wherein the protein in A) has DNA polymerase activity.

In some embodiments, the protein in A) has amino acid modifications at positions 408, 409 and 485, and at least three of amino acid modifications at positions 53, 59, 199, 243, 526, 558, 613, 641, 671, 673, 674, 692 and 709 compared to the amino acid sequence of the wild-type KOD DNA polymerase, wherein the protein in A) has DNA polymerase activity.

In some embodiments, the modification is substitution of an amino acid.

In some embodiments, leucine at position 408 is substituted with isoleucine, tyrosine, proline, valine, cysteine, serine, alanine or methionine;

tyrosine at position 409 is substituted with alanine or glycine;

alanine at position 485 is substituted with histidine, asparagine, lysine, aspartic acid or glutamic acid; and at least one of amino acid(s) at positions 53, 59, 199, 243, 526, 558, 613, 641, 671, 673, 674, 692 and 709 is/are substituted with methionine, phenylalanine or alanine.

In some embodiments, substituting the at least one of amino acid(s) at positions 53, 59, 199, 243, 526, 558, 613, 641, 671, 673, 674, 692 and 709 with methionine, phenylalanine or Alanine includes:
  substitution of lysine at position 53 with methionine;
  substitution of histidine at position 59 with phenylalanine;
  substitution of lysine at position 199 with methionine;
  substitution of arginine at position 243 with methionine;
  substitution of lysine at position 526 with methionine;
  substitution of lysine at position 558 with methionine;
  substitution of arginine at position 613 with methionine;
  substitution of arginine at position 641 with methionine;
  substitution of lysine at position 671 with methionine;
  substitution of tyrosine at position 673 with phenylalanine;
  substitution of lysine at position 674 with alanine;
  substitution of lysine at position 692 with methionine; and
  substitution of arginine at position 709 with methionine.

In some embodiments, the protein has a lower adsorption capacity for a biochip compared to the wild-type KOD DNA polymerase. The lower adsorption capacity for the biochip is reflected in that the protein is poor at adsorption on the surface of the biochip and/or is easy to be eluted from the surface of the biochip.

In some embodiments, A DNA molecule encoding the protein described above is within the scope of the present disclosure; or an expression kit, a recombinant expression vector, a recombinant bacteria or a transgenic cell line containing the DNA molecule described above are also within the scope of the present disclosure.

In some embodiments, use of the protein, the DNA molecule, the expression kit, the recombinant expression vector, the recombinant bacteria or the transgenic cell line described above for preparing a DNA polymerase is also within the scope of the present disclosure. According to the embodiment, the DNA polymerase prepared by the protein, the DNA molecule, the expression kit, the recombinant expression vector, the recombinant bacteria or the transgenic cell line has a lower adsorption capacity for a biochip compared to a wild-type KOD DNA polymerase; and the lower adsorption capacity for the biochip is reflected in that the DNA polymerase prepared is poorer at adsorption on the surface of the biochip and/or is easier to be eluted from the surface of the biochip compared to the wild-type KOD DNA polymerase. According to the embodiment, the protein served as a DNA polymerase is characterized by a high polymerization activity and/or a low adsorption for a biochip when a single-stranded DNA is used as a template. According to the embodiment, a polymerization reaction between the protein served as a DNA polymerase and the single-stranded DNA is conducted on a biochip. The biochip described above can be any biochip commonly used in the art.

In some embodiments, use of the protein, the DNA molecule, the expression kit, the recombinant expression vector, the recombinant bacteria or the transgenic cell line described above in sequencing is within the scope of the present disclosure; or use of the protein, the DNA molecule, the expression kit, the recombinant expression vector, the recombinant bacteria or the transgenic cell line described above in preparing a product for sequencing is also within the scope of the present disclosure. According to the embodiment, the use described above, the product is a kit.

In some embodiments, a substrate of the protein served as a DNA polymerase is a nucleotide or its analogs. A template for the protein served as a DNA polymerase is a single-stranded DNA.

In some embodiments, the protein described above also refers to a variant protein of KOD DNA polymerase, specifically including: a KOD DNA polymerase variant, including Ue1A, Ue1B, Ue1C, Ue1D, Ue1E, Ue2A, Ue2B, Ue2C, Ue2D, Ue2E, Ue3A, Ue3B, Ue3C, Ue3D, Ue3E, Ue4A, Ue4B, Ue4C, Ue1A5, Ue1A6, Ue1B5, Ue1B6, Ue1C5, Ue1C6, Ue1D5, Ue1D6, Ue1E5, Ue1E6, Ue2A5, Ue2A6, Ue2B5, Ue2B6, Ue2C5, Ue2C6, Ue2D5, Ue2D6, Ue2E5, Ue2E6, Ue3A5, Ue3A6, Ue3B5, Ue3B6, Ue3C5, Ue3C6, Ue3D5, Ue3D6, Ue3E5, Ue3E6, Ue4A5, Ue4A6, Ue4B5, Ue4B6, Ue4C5 and Ue4C6, and a C-terminal shortened KOD DNA polymerase variant, being the KOD DNA polymerase variant described above of which amino acids 1 to 29 from the C-terminus is deleted and the remaining amino acids are kept unchanged.

In some embodiments, a KOD DNA polymerase variant refers to a protein having amino acid mutations at positions 408, 409 and 485, and at least one of amino acid mutation(s) at positions 53, 59, 199, 243, 526, 558, 613, 641, 671, 673, 674, 692 and 709 compared to the amino acid sequence of a wild-type KOD DNA polymerase depicted in SEQ ID NO: 1. The specific variants in the present disclosure are shown below.

Ue1A, has an amino acid sequence which includes a mutation at position 408 from leucine to isoleucine, a mutation at position 409 from tyrosine to alanine, and a mutation at position 485 from alanine to histidine compared to the amino acid sequence depicted in SEQ ID NO: 1;

Ue1B, has an amino acid sequence which includes a mutation at position 408 from leucine to isoleucine, a mutation at position 409 from tyrosine to alanine, and a mutation at position 485 from alanine to asparagine compared to the amino acid sequence depicted in SEQ ID NO: 1;

Ue1C, has an amino acid sequence which includes a mutation at position 408 from leucine to isoleucine, a mutation at position 409 from tyrosine to alanine, and a mutation at position 485 from alanine to lysine compared to the amino acid sequence depicted in SEQ ID NO: 1;

Ue1D, has an amino acid sequence which includes a mutation at position 408 from leucine to isoleucine, a mutation at position 409 from tyrosine to alanine, and a mutation at position 485 from alanine to aspartic acid compared to the amino acid sequence depicted in SEQ ID NO: 1;

Ue1E, has an amino acid sequence which includes a mutation at position 408 from leucine to isoleucine, a mutation at position 409 from tyrosine to alanine, and a mutation at position 485 from alanine to glutamic acid compared to the amino acid sequence depicted in SEQ ID NO: 1;

Ue2A, has an amino acid sequence which includes a mutation at position 408 from leucine to alanine, a mutation at position 409 from tyrosine to alanine, and a mutation at position 485 from alanine to histidine compared to the amino acid sequence depicted in SEQ ID NO: 1;

Ue2B, has an amino acid sequence which includes a mutation at position 408 from leucine to alanine, a mutation at position 409 from tyrosine to alanine, and a mutation at position 485 from alanine to asparagine compared to the amino acid sequence depicted in SEQ ID NO: 1;

Ue2C, has an amino acid sequence which includes a mutation at position 408 from leucine to alanine, a mutation at position 409 from tyrosine to alanine, and a mutation at position 485 from alanine to lysine compared to the amino acid sequence depicted in SEQ ID NO: 1;

Ue2D, has an amino acid sequence which includes a mutation at position 408 from leucine to alanine, a mutation at position 409 from tyrosine to alanine, and a mutation at position 485 from alanine to aspartic acid compared to the amino acid sequence depicted in SEQ ID NO: 1;

Ue2E, has an amino acid sequence which includes a mutation at position 408 from leucine to alanine, a mutation at position 409 from tyrosine to alanine, and a mutation at position 485 from alanine to glutamic acid compared to the amino acid sequence depicted in SEQ ID NO: 1;

Ue3A, has an amino acid sequence which includes a mutation at position 408 from leucine to valine, a mutation at position 409 from tyrosine to alanine, and a mutation at position 485 from alanine to histidine compared to the amino acid sequence depicted in SEQ ID NO: 1;

Ue3B, has an amino acid sequence which includes a mutation at position 408 from leucine to valine, a mutation at position 409 from tyrosine to alanine, and a mutation at position 485 from alanine to asparagine compared to the amino acid sequence depicted in SEQ ID NO: 1;

Ue3C, has an amino acid sequence which includes a mutation at position 408 from leucine to valine, a mutation at position 409 from tyrosine to alanine, and a mutation at position 485 from alanine to lysine compared to the amino acid sequence depicted in SEQ ID NO: 1;

Ue3D, has an amino acid sequence which includes a mutation at position 408 from leucine to valine, a mutation at position 409 from tyrosine to alanine, and a mutation at position 485 from alanine to aspartic acid compared to the amino acid sequence depicted in SEQ ID NO: 1;

Ue3E, has an amino acid sequence which includes a mutation at position 408 from leucine to valine, a mutation at position 409 from tyrosine to alanine, and a mutation at position 485 from alanine to glutamic acid compared to the amino acid sequence depicted in SEQ ID NO: 1;

Ue4A, has an amino acid sequence which includes a mutation at position 408 from leucine to serine, a mutation at position 409 from tyrosine to alanine, and a mutation at position 485 from alanine to histidine compared to the amino acid sequence depicted in SEQ ID NO: 1;

Ue4B, has an amino acid sequence which includes a mutation at position 408 from leucine to serine, a mutation at position 409 from tyrosine to alanine, and a mutation at position 485 from alanine to asparagine compared to the amino acid sequence depicted in SEQ ID NO: 1;

Ue4C, has an amino acid sequence which includes a mutation at position 408 from leucine to serine, a mutation at position 409 from tyrosine to alanine, and a mutation at position 485 from alanine to lysine compared to the amino acid sequence depicted in SEQ ID NO: 1;

Ue1A5, has an amino acid sequence which includes a mutation at position 408 from leucine to isoleucine, a mutation at position 409 from tyrosine to alanine, a mutation at position 485 from alanine to histidine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine and a mutation at position 709 from arginine to methionine compared to the amino acid sequence depicted in SEQ ID NO: 1;

Ue1A6, has an amino acid sequence which includes a mutation at position 408 from leucine to isoleucine, a mutation at position 409 from tyrosine to alanine, a mutation at position 485 from alanine to histidine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue1B5, has an amino acid sequence which includes a mutation at position 408 from leucine to isoleucine, a mutation at position 409 from tyrosine to alanine, a mutation at position 485 from alanine to asparagine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue1B6, has an amino acid sequence which includes a mutation at position 408 from leucine to isoleucine, a mutation at position 409 from tyrosine to alanine, a mutation at position 485 from alanine to asparagine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue1C5, has an amino acid sequence which includes a mutation at position 408 from leucine to isoleucine, a mutation at position 409 from tyrosine to alanine, a mutation at position 485 from alanine to lysine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine, compared to the amino acid sequence depicted in SEQ ID NO: 1;

Ue1C6, has an amino acid sequence which includes a mutation at position 408 from leucine to isoleucine, a mutation at position 409 from tyrosine to alanine, a mutation at position 485 from alanine to lysine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue1D5, has an amino acid sequence which includes a mutation at position 408 from leucine to isoleucine, a mutation at position 409 from tyrosine to alanine, a mutation at position 485 from alanine to aspartic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine, compared to the amino acid sequence depicted in SEQ ID NO: 1;

Ue1D6, has an amino acid sequence which includes a mutation at position 408 from leucine to isoleucine, a mutation at position 409 from tyrosine to alanine, a mutation at position 485 from alanine to aspartic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue1E5, has an amino acid sequence which includes a mutation at position 408 from leucine to isoleucine, a mutation at position 409 from tyrosine to alanine, a mutation at position 485 from alanine to glutamic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue1E6, has an amino acid sequence which includes a mutation at position 408 from leucine to isoleucine, a mutation at position 409 from tyrosine to alanine, a mutation at position 485 from alanine to glutamic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue2A5, has an amino acid sequence which includes a mutation at position 408 from leucine to alanine, a mutation at position 409 from tyrosine to alanine, a mutation at position 485 from alanine to histidine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue2A6, has an amino acid sequence which includes a mutation at position 408 from leucine to alanine, a mutation at position 409 from tyrosine to alanine, a mutation at position 485 from alanine to histidine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue2B5, has an amino acid sequence which includes a mutation at position 408 from leucine to alanine, a mutation at position 409 from tyrosine to alanine, a mutation at position 485 from alanine to asparagine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue2B6, has an amino acid sequence which includes a mutation at position 408 from leucine to alanine, a mutation at position 409 from tyrosine to alanine, a mutation at position 485 from alanine to asparagine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue2C5, has an amino acid sequence which includes a mutation at position 408 from leucine to alanine, a mutation at position 409 from tyrosine to alanine, a mutation at position 485 from alanine to lysine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue2C6, has an amino acid sequence which includes a mutation at position 408 from leucine to alanine, a mutation at position 409 from tyrosine to alanine, a mutation at position 485 from alanine to lysine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue2D5, has an amino acid sequence which includes a mutation at position 408 from leucine to alanine, a mutation at position 409 from tyrosine to alanine, a mutation at position 485 from alanine to aspartic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue2D6, has an amino acid sequence which includes a mutation at position 408 from leucine to alanine, a mutation at position 409 from tyrosine to alanine, a mutation at position 485 from alanine to aspartic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue2E5, has an amino acid sequence which includes a mutation at position 408 from leucine to alanine, a mutation at position 409 from tyrosine to alanine, a mutation at position 485 from alanine to glutamic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue2E6, has an amino acid sequence which includes a mutation at position 408 from leucine to alanine, a mutation at position 409 from tyrosine to alanine, a mutation at position 485 from alanine to glutamic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue3A5, has an amino acid sequence which includes a mutation at position 408 from leucine to valine, a mutation at position 409 from tyrosine to alanine, a mutation at position 485 from alanine to histidine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue3A6, has an amino acid sequence which includes a mutation at position 408 from leucine to valine, a mutation at position 409 from tyrosine to alanine, a mutation at position 485 from alanine to histidine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue3B5, has an amino acid sequence which includes a mutation at position 408 from leucine to valine, a mutation at position 409 from tyrosine to alanine, a mutation at position 485 from alanine to asparagine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue3B6, has an amino acid sequence which includes a mutation at position 408 from leucine to valine, a mutation at position 409 from tyrosine to alanine, a mutation at position 485 from alanine to asparagine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue3C5, has an amino acid sequence which includes a mutation at position 408 from leucine to valine, a mutation at position 409 from tyrosine to alanine, a mutation at position 485 from alanine to lysine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue3C6, has an amino acid sequence which includes a mutation at position 408 from leucine to valine, a mutation at position 409 from tyrosine to alanine, a mutation at position 485 from alanine to lysine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue3D5, has an amino acid sequence which includes a mutation at position 408 from leucine to valine, a mutation at position 409 from tyrosine to alanine, a mutation at position 485 from alanine to aspartic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue3D6, has an amino acid sequence which includes a mutation at position 408 from leucine to valine, a mutation at position 409 from tyrosine to alanine, a mutation at position 485 from alanine to aspartic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue3E5, has an amino acid sequence which includes a mutation at position 408 from leucine to valine, a mutation at position 409 from tyrosine to alanine, a mutation at position 485 from alanine to glutamic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue3E6, has an amino acid sequence which includes a mutation at position 408 from leucine to valine, a mutation at position 409 from tyrosine to alanine, a mutation at position 485 from alanine to glutamic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue4A5, has an amino acid sequence which includes a mutation at position 408 from leucine to serine, a mutation at position 409 from tyrosine to alanine, a mutation at position 485 from alanine to histidine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue4A6, has an amino acid sequence which includes a mutation at position 408 from leucine to serine, a mutation at position 409 from tyrosine to alanine, a mutation at position 485 from alanine to histidine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue4B5, has an amino acid sequence which includes a mutation at position 408 from leucine to serine, a mutation at position 409 from tyrosine to alanine, a mutation at position 485 from alanine to asparagine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1;

Ue4B6, has an amino acid sequence which includes a mutation at position 408 from leucine to serine, a mutation at position 409 from tyrosine to alanine, a mutation at position 485 from alanine to asparagine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1;

Ue4C5, has an amino acid sequence which includes a mutation at position 408 from leucine to serine, a mutation at position 409 from tyrosine to alanine, a mutation at position 485 from alanine to lysine, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1; and Ue4C6, has an amino acid sequence which includes a mutation at position 408 from leucine to serine, a mutation at position 409 from tyrosine to alanine, a mutation at position 485 from alanine to lysine, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1.

In some embodiments, a tag can be added to the N-terminus or C-terminus of the amino acid sequence of the KOD DNA polymerase variants of the present disclosure for purification, and the presence or absence of the tag does not affect the property of the KOD DNA polymerase variants as known in the art, in which the tag is generally selected from those shown in Table 1.

TABLE 1

| Tag and its sequence for enzyme | | |
|---|---|---|
| Tag(s) | number | sequence |
| Poly-Arg | 5-6, general 5 | RRRRR |
| Poly-His | 2-10, general 6 | HHHHHH |
| FLAG | 8 | DYKDDDDK |
| Strep-tag II | 8 | WSHPQFEK |
| c-myc | 10 | EQKLISEEDL |

In some embodiments, the fusion proteins of the KOD DNA polymerase variants of the present disclosure each connect with 6 His-tags at the C-terminus, and alternatively such the KOD DNA polymerase variants also may not connect with the tag at the C-terminus as known to the skilled in the art.

It should be noted, fusion proteins of the KOD DNA polymerase variants with the His-tag are each of an amino acid sequence which has 6 His-tags at the C-terminus compared to the amino acid sequence of the corresponding KOD DNA polymerase variant as described in some embodiments of the present disclosure. The encoding genes of the fusion proteins of the KOD DNA polymerase variants with the His-tag are each of a nucleotide sequence which has codons of 6 His-tags at its 3' end compared to the nucleotide sequence of the corresponding KOD DNA polymerase variant.

In some embodiments, the C-terminal shortened KOD DNA polymerase variant is the KOD DNA polymerase variant described above of which amino acids 1 to 29 from the C-terminus was deleted. According to some embodiments, the specific C-terminal shortened KOD DNA polymerase variants in the present disclosure includes Ue1A, Ue1B, Ue1C, Ue1D, Ue1E, Ue2A, Ue2B, Ue2C, Ue2D, Ue2E, Ue3A, Ue3B, Ue3C, Ue3D, Ue3E, Ue4A, Ue4B and Ue4C6.

Specifically, amino acids 1 to 29 from the C-terminus of each of the variants described above are deleted, and thus obtaining the corresponding C-terminal shortened KOD DNA polymerase variants, which are named as ΔUe1A, ΔUe1B, ΔUe1C, ΔUe1D, ΔUe1E, ΔUe2A, ΔUe2B, ΔUe2C, ΔUe2D, ΔUe2E, ΔUe3A, ΔUe3B, ΔUe3C, ΔUe3D, ΔUe3E, ΔUe4A, ΔUe4B and ΔUe4C respectively.

According to some embodiments, the fusion proteins of the C-terminal shortened KOD DNA polymerase variants are the C-terminal shortened KOD DNA polymerase variants described above which each connect with 6 His-tags at the C-terminus respectively.

In a specific embodiment, the KOD DNA polymerase variant Ue1E has an amino acid sequence as depicted in SEQ ID NO: 8 which includes a mutation at position 408 from leucine to isoleucine, a mutation at position 409 from tyrosine to alanine, and a mutation at position 485 from alanine to glutamic acid compared to the amino acid sequence depicted in SEQ ID NO: 1; and the encoding gene of Ue1E has a nucleotide sequence as depicted in SEQ ID NO: 9 which includes a mutation at position 1222 from cytosine (C) to adenine (A), a mutation at position 1224 from guanine (G) to thymine (T), a mutation at position 1225 from thymine (T) to guanine (G), a mutation at position 1226 from adenine (A) to cytosine (C), a mutation at position 1227 from thymine (T) to adenine (A) and a mutation at position 1454 from cytosine (C) to adenine (A), compared to the nucleotide sequence depicted in SEQ ID NO: 2.

In a specific embodiment, the KOD DNA polymerase variant Ue1E5 has an amino acid sequence as depicted in SEQ ID NO: 10 which includes a mutation at position 408 from leucine to isoleucine, a mutation at position 409 from tyrosine to alanine, a mutation at position 485 from alanine to glutamic acid, a mutation at position 53 from lysine to methionine, a mutation at position 199 from lysine to methionine, a mutation at position 243 from arginine to methionine, a mutation at position 526 from lysine to methionine, a mutation at position 674 from lysine to alanine, and a mutation at position 709 from arginine to methionine compared to the amino acid sequence depicted in SEQ ID NO: 1; and the encoding gene of Ue1E5 has a nucleotide sequence as depicted in SEQ ID NO: 11 which includes a mutation at position 1222 from cytosine (C) to adenine (A), a mutation at position 1224 from guanine (G) to thymine (T), a mutation at position 1225 from thymine (T) to guanine (G), a mutation at position 1226 from adenine (A) to cytosine (C), a mutation at position 1227 from thymine (T) to adenine (A), a mutation at position 1454 from cytosine (C) to adenine (A), a mutation at position 158 from adenine (A) to thymine (T), a mutation at position 159 from adenine (A) to guanine (G), a mutation at position 596 from adenine (A) to thymine (T), a mutation at position 597 with guanine (G), a mutation at position 727 from cytosine (C) to adenine (A), a mutation at position 728 from guanine (G) to thymine (T), a mutation at position 729 from cytosine (C) to guanine (G), a mutation at position 1577 from adenine (A) to thymine (T), a mutation at position 1578 from adenine (A) to guanine (G), a mutation at position 2021 from adenine (A) to thymine (T), a mutation at position 2125 from cytosine (C) to guanine (G), a mutation at position 2126 from guanine (G) to thymine (T), and a mutation at position 2127 from thymine (T) to guanine (G), compared to the nucleotide sequence depicted in SEQ ID NO: 2.

In a specific embodiment, the KOD DNA polymerase variant Ue1E6, has an amino acid sequence as depicted in SEQ ID NO: 12 which includes a mutation at position 408 from leucine to isoleucine, a mutation at position 409 from tyrosine to alanine, a mutation at position 485 from alanine to glutamic acid, a mutation at position 59 from histidine to phenylalanine, a mutation at position 558 from lysine to methionine, a mutation at position 613 from arginine to methionine, a mutation at position 641 from arginine to methionine, a mutation at position 671 from lysine to methionine, a mutation at position 673 from tyrosine to phenylalanine, and a mutation at position 692 from lysine to methionine compared to the amino acid sequence depicted in SEQ ID NO: 1; and the encoding gene of Ue1E6 has a nucleotide sequence as depicted in SEQ ID NO: 13 which includes a mutation at position 1222 from cytosine (C) to adenine (A), a mutation at position 1224 from guanine (G) to thymine (T), a mutation at position 1225 from thymine (T) to guanine (G), a mutation at position 1226 from adenine (A) to cytosine (C), a mutation at position 1227 from thymine (T) to adenine (A), a mutation at position 1454 from cytosine (C) to adenine (A), a mutation at position 175 from cytosine (C) to thymine (T), a mutation at position 176 from adenine (A) to thymine (T), a mutation at position 1673 from adenine (A) to thymine (T), a mutation at position 1674 from adenine (A) to guanine (G), a mutation at position 1837 from cytosine (C) to adenine (A), a mutation at position 1838 from guanine (G) to thymine (T), a mutation at position 1839 from thymine (T) to guanine (G), a mutation at position 1921 from cytosine (C) to adenine (A), a mutation at position 1922 from guanine (G) to thymine (T), a mutation at position 1923 from thymine (T) to guanine (G), a mutation at position 2012 from adenine (A) to thymine (T), a mutation at position 2013 from adenine (A) to guanine (G), a mutation at position 2018 from adenine (A) to thymine (T), and a mutation at position 2075 from adenine (A) to thymine (T), compared to the nucleotide sequence depicted in SEQ ID NO: 2.

EXAMPLES

Example 1. Preparation of Wild-Type KOD DNA Polymerase and its Variants

In this example, an expressing vectors of the wild-type KOD DNA polymerase and its variants are constructed by using Electra™ Cloning Reagents Kit (DNA 2.0), with a His-tag for affinity purification on a Ni column.

1.1 Preparation of Fusion Protein of Wild-Type KOD DNA Polymerase

The wild-type KOD DNA polymerase is of an amino acid sequence as depicted in SEQ ID NO: 1, which is encoded by its encoding gene having a nucleotide sequence as depicted in SEQ ID NO: 2.

1.1.1 Construction of Recombinant Expression Vector pD441-WT

A fusion protein of the wild-type KOD DNA polymerase with a His-tag is of an amino acid sequence which connects with 6 His-tags at its C-terminus compared to the amino acid sequence of the wild-type KOD DNA polymerase as depicted in SEQ ID NO:1.

The encoding gene of the fusion protein of the wild-type KOD DNA polymerase with the His-tag is of a nucleotide sequence which connects with codons of 6 His-tags at its 3' end compared to the nucleotide sequence of the wild-type KOD DNA polymerase as depicted in SEQ ID NO:2.

The recombinant expression vector pD441-WT was obtained by recombining the encoding gene of the fusion protein of the wild-type KOD DNA polymerase with the His-tag into the vector pD441-pelB (DNA2.0, pD441-pelB) according to the instruction of Electra™ Cloning Reagents Kit (DNA2.0, EKT-02), where the expression of such the encoding gene was directed by a signal peptide of the vector pD441-pelB.

1.1.2 Construction of Recombinant Bacteria

After transfected with the recombinant expression vector pD441-WT, the *E. coli* BL21 competent cells purchased from TransGen Biotech were plated into a petri dish containing culture medium with 50 μg/mL kanamycin to screen positive colonies which contain a target recombinant expression vector (i.e. that contains the encoding gene of the fusion protein of the wild-type KOD DNA polymerase with His-tag). 3 to 5 positive colonies picked out were subjected to the colony PCR amplification under a pair of primers (i.e. SQF depicted in SEQ ID NO:3, and SQR depicted in SEQ ID NO:4) to identify the presence of the target recombinant expression vector, thus obtaining the positive colony loaded with the encoding gene in a length of 2800 bp identical to the theoretical value expected and named as the positive colony BL21/pD441-WT.

1.1.3 Expression and Purification of Fusion Protein of Wild-Type KOD DNA Polymerase A single positive colony BL21/pD441-WT picked out was inoculated in 50 mL LB liquid culture medium containing 50 μg/mL kanamycin for culture at 37° C. overnight, with 220 rpm/min of shaking. In the next day, the bacteria solution in a 1:100 dilution was transferred to 1000 mL LB liquid culture medium with 50 μg/mL kanamycin and cultured at the same condition until the value of OD600 reaches 0.5 to 0.8. After that, an inducer Isopropyl 0-D-Thiogalactoside (IPTG) in a final concentration of 0.5 mM was added to induce the expression of recombinant expression vector, and the bacteria solution was still cultured at 25° C. overnight, followed that the bacteria solution BL21/pD441-WT containing the expressed fusion protein of the wild-type KOD DNA polymerase with His-tag was harvested, while the bacteria solution without the inducer IPTG was used as a blank control, and the corresponding uninduced bacteria solution BL21/pD441-WT was also collected.

The induced bacterial solution BL21/pD441-WT was centrifuged at 8000 rpm/min for 10 min, followed by removing the supernatant, thus obtaining the precipitated pellets. The bacterial pellets were subsequently resuspended in a first buffer (including 50 mMKPO$_4$, 500 mM NaCl, 10 mM imidazole and 5% Glycerol, PH 7.0), to which phenylmethanesulfonyl fluoride (PMSF) in a final concentration of 0.5 mM, Triton X-100 in a final concentration of 0.5% and Lysozyme in a final concentration of 0.25% were added, followed by incubating at room temperature for 30 minutes. After that, the bacterial solution was subjected to centrifugation at 12000 rpm/min and 4° C. for another 30 min, an ice bath, ultrasonication to break bacterial cells, and centrifugation at 12000 rpm/min for further 30 min, with the supernatant collected warming in a water bath of 75° C. for 20 minutes, during which mixing was taken after a definite time period to ensure uniform heating. After centrifugation at 12000 rpm/min and 4° C. for 30 min, the supernatant was filtered through a 0.22 um filter to obtain a crude fusion protein.

The crude fusion protein was loaded into a Ni column for affinity chromatography (HisTrap FF, 5 mL, 17-5255-01, GE healthcare) at a suitable flow rate, after which 5 column volumes (CVs) of the first buffer was loaded for equilibration, and 5 CVs of a second buffer in 3% (including 50 mMKPO$_4$, 1M NaCl and 5% Glycerol, PH 7.0) loaded for a first elution, 5 CVs of the second buffer in 50% loaded for a second elution, with collection of the eluate of the Ni column corresponding to a peak value of 100 mAU or above.

The eluate corresponding to the peak value of 100 mAU or above was loaded into an ion exchange column (HiTrap Q HP, 5 mL, 17-1154-01, GE healthcare) at a suitable flow rate, after which 5 CVs of the second buffer was loaded for equilibration, and the second buffer from 0% to 60% loaded for a linear elution, with collection of the eluate of ion exchange chromatography corresponding to a peak value of 100 mAU or above.

The eluate of ion exchange chromatography corresponding to the peak value of 100 mAU or above was loaded into a gel chromatography column (HiPrep Sephacryl S-100 HR, 26 mm, 17-1194-01, GE healthcare), where the gel chromatography column was washed with 3 CVs of 20% ethanol and 3 CVs of water, and equilibrated with 3 CVs of a third buffer in 100% (including 20 mM Tris, 200 mM KCl, 0.2 mM EDTA and 10% Glycerol, PH7.4) before loaded with the eluate. After that, 1.5 CVs of the third buffer was loaded for elution, with the eluate (that is a purified fusion protein) collected.

The purified fusion protein of the wild-type KOD DNA polymerase was detected to be a yield of 40 mg/L.

The purified fusion protein of the wild-type KOD DNA polymerase was subjected to SDS-PAGE gel electrophoresis (where 5% of concentrated gel and 12% of separation gel were used). The results are shown in FIG. 1, in which Lane 1 represents a marker (PageRuler Prestained Protein Ladder, 26616, Thermo Scientific), Lane 2 represents a mixture of the purified fusion protein of the wild-type KOD DNA polymerase (1 mg/mL, 10 μL) and 2× loading buffer (10 μL), and Lane 3 represents a mixture of the purified fusion protein of the wild-type KOD DNA polymerase (0.05 mg/mL, 10 μL) and 2× loading buffer (10 μL), and it can be seen that the protein occurring in Lane 2 and Lane 3 is of a molecular weight about 91.5 KDa respectively, which is consistent with that reported in a literature.

The gel containing the purified fusion protein after gel electrophoresis was taken and detected by the Quantity one software for purity, and the result shows that the purity of the purified fusion protein is 95% or above.

This example also shows that no purified fusion protein in a molecular weight of about 91.5 KDa is present in the uninduced bacterial solution BL21/pD441-WT which is used as a positive control.

In this example, an empty vector pD441-pelB without the recombinant expression vector pD441-WT was also transfected into *E. coli* BL21 as a negative control, with a negative colony BL21/pD441-pelB was obtained, which was then subjected to protein expression and purification as the method described in 1.1.3, and no purified fusion protein in a molecular weight of about 91.5 KDa was detected similarly.

1.2 Preparation of Fusion Protein of KOD DNA Polymerase Variant 1.2.1 Construction of Recombinant Expression Vector of KOD DNA Polymerase Variant The recombinant expression vectors of different KOD DNA polymerase variants were constructed by recombing the encoding genes of the fusion proteins of different KOD DNA polymerase variants with a His-tag into the vector pD441-pelB (DNA2.0, pD441-pelB) respectively as the method described in step 1.1.1 above, thus obtaining individual recombinant expression vectors of different KOD DNA polymerase variants with the His-tag. The expression of such the encoding gene was directed by a signal peptide of the vector pD441-pelB.

1.2.2 Construction of Recombinant Bacteria

Similar to the method described in 1.1.2, the recombinant expression vectors of the KOD DNA polymerase variants constructed above were respectively transfected into *E. coli* BL21 competent cells, thus obtaining positive colonies capable of expressing the fusion proteins of different KOD DNA polymerase variants respectively.

1.2.3 Expression and Purification of Fusion Protein of KOD DNA Polymerase Variant Similar to the method described in 1.1.3, the positive colonies expressing the fusion proteins of the KOD DNA polymerase variants were cultured, and the fusion proteins generated were purified through chromatography methods, thus obtaining purified fusion proteins of KOD DNA polymerase variants.

The purified fusion proteins of KOD DNA polymerase variants were detected for purity as the method in 1.1.3, and the result shows that the purity of the purified fusion proteins are all 95% or above.

1.3 Preparation of Fusion Protein of C-Terminal Shortened KOD DNA Polymerase Variant The C-terminal shortened KOD DNA polymerase variant is the KOD DNA polymerase variant prepared in 1.2 above of which 29 amino acids at a C-terminal region was deleted. Specifically, amino acids 1 to 29 from the C-terminus of each of variants (including Ue1A, Ue1B, Ue1C, Ue1D, Ue1E, Ue2A, Ue2B, Ue2C, Ue2D, Ue2E, Ue3A, Ue3B, Ue3C, Ue3D, Ue3E, Ue4A, Ue4B and Ue4C) were deleted, and thus obtaining the corresponding C-terminal shortened KOD DNA polymerase variants, which are named as ΔUe1A, ΔUE1B, ΔUe1C, ΔUe2A, ΔUe2B, ΔUe2C, ΔUe2D, ΔUe2E, ΔUe3A, ΔUe3B, ΔUe3C, ΔUe3D, ΔUe3E, ΔUe4A, ΔUe4B and ΔUe4C.

The fusion proteins of the C-terminal shortened KOD DNA polymerase variants are the C-terminal shortened KOD DNA polymerase variants described above which each connect with 6 His-tags at the C-terminus respectively.

The fusion proteins of the C-terminal shortened KOD DNA polymerase variants were prepared similar to the method in 1.2, and the purity of them was identified to be 95% or above.

Example 2. Characterization of Fusion Protein of KOD DNA Polymerase Variant

The fusion proteins of KOD DNA polymerase variants in this example are all those prepared according to method 1.2 above, which respectively contain 6 His-tags at the C-terminus.

2.1 Polymerization Activity Assay of Fusion Protein of KOD DNA Polymerase Variant The fusion proteins of KOD DNA polymerase variants were detected for polymerization activity according to the procedure described in Nishioka, M., et al. (2001. J. Biotechnol. 88), where one enzyme unit (U) was defined as the amount of enzyme (i.e. the fusion protein of KOD DNA polymerase variant) required for converting 10 nmol dNTP to an acid insoluble material in 30 minutes at 75° C. and a 50 μL reaction system.

The reaction system for the wild-type KOD DNA polymerase includes 20 mM Tris-HCl (pH 7.5), 8 mM MgCl$_2$, 50 μg/mL BSA, 0.15 mM each dNTPs (dATP, dTTP, dCTP and dGTP), [methyl-3H]-TTP (0.13 mCi/nmol), 150 mg/mL activated calf thymus, 7.5 mM DTT, and 1 μL wild-type KOD DNA polymerase (1 mg/mL). The reaction system is of a total reaction volume of 50 μL.

The wild-type KOD DNA polymerase was used as a control.

The reaction system above was incubated at 75° C. for 30 minutes, and the polymerization activity of the wild-type KOD DNA polymerase was calculated to be 2 U/μL according to the definition above.

The fusion protein of wild-type KOD DNA polymerase and fusion proteins of KOD DNA polymerase variants were assayed according to the method described above.

KOD DNA polymerase variant Ue1E, Ue1E5 and Ue1E6 were detected in this example.

The results of polymerization activity of the KOD DNA polymerase variant are shown in Table 2. It can be seen that the variant has DNA polymerization activity.

TABLE 2 polymerization activity of KOD DNA polymerase variant

| Names | Polymerization activity | Mutation position | Amino acid after mutation |
|---|---|---|---|
| Wild-type KOD DNA polymerase | 2 U/μL | None | None |
| Variant Ue1E | 1 U/μL | 408, 409, 485 | Isoleucine at position 408, Alanine at position 409, glutamic acid at position 485 |
| Variant Ue1E5 | 1.2 U/μL | 408, 409, 485, 53, 199, 243, 526, 674, 709 | Isoleucine at position 408, Alanine at position 409, glutamic acid at position 485, methionine at position 53, methionine at position 199, methionine at position 243, methionine at position 526, alanine at position 674, methionine at position 709 |
| Variant Ue1E6 | 1.7 U/μL | 408, 409, 485, 59, 558, 613, 641, 671, 673, 692 | Isoleucine at position 408, Alanine at position 409, glutamic acid at position 485, phenylalanine at position 59, methionine at position 558, methionine at position 613, methionine at position 641, methionine at position 671, phenylalanine at position 673, methionine at position 692 |

The results of polymerization activity of other variants, such as Ue1A, Ue1B, Ue1C, Ue1D, Ue2A, Ue2B, Ue2C, Ue2D, Ue2E, Ue3A, Ue3B, Ue3C, Ue3D, Ue3E, Ue4A, Ue4B, Ue4C, Ue1A5, Ue1A6, Ue1B5, Ue1B6, Ue1C5, Ue1C6, Ue1D5, Ue1D6, Ue2A5, Ue2A6, Ue2B5, Ue2B6, Ue2C5, Ue2C6, Ue2D5, Ue2D6, Ue2E5, Ue2E6, Ue3A5, Ue3A6, Ue3B5, Ue3B6, Ue3C5, Ue3C6, Ue3D5, Ue3D6, Ue3E5, Ue3E6, Ue4A5, Ue4A6, Ue4B5, Ue4B6, Ue4C5 and Ue4C6 are similar to the variant Ue1E, Ue1E5 or Ue1E6.

2.2 Michaelis-Menten Kinetics of Fusion Protein of KOD DNA Polymerase Variant

In this example, the relative reaction rate of the fusion protein of the KOD DNA polymerase variant was measured by using a Cy3 fluorescent dye-labeled dATP (i.e. dATP-Cy3) and a DNA template labeled with Cy5 fluorescent dye (i.e. DNA template-Cy5), with a microplate reader detecting a fluorescence value, by which the Michaelis-Menten kinetics curve is depicted, thus obtaining a Km value and Kcat/Km of each variant. The special experimental method is as below.

Specifically, a DNA template depicted in SEQ ID NO:7 synthesized by Genscript company was mixed with a pair of primer labeled with 5'Cy5 fluorescent dye (S1A depicted in SEQ ID NO:5, and S2A depicted in SEQ ID NO:6) in an equimolar of 1:1:1, followed by annealing at 65° C. for 1 minute, at 40° C. for 1 minute and at 4° C. for 10 minutes, with the DNA product annealed (i.e. the DNA template-Cy5 labeled with Cy5 fluorescent dye) stored at −20° C. in the dark.

The enzymatic reaction was performed by incubating a reaction system in a 384-well plate (Corning black, clear bottom 384-well plate), with the BioTek microplate reader detecting the result of enzyme activity. The reaction system is of a total reaction volume of 50 μL per well.

The reaction system for KOD DNA polymerase variant includes 2U fusion protein of KOD DNA polymerase variant, dNTPs (1 μM dATP-Cy3, 10 μM dTTP, 10 μM dCTP and 10 μM dGTP), the DNA template-Cy5 and an enzyme reaction buffer in a pH 8.8. The Michaelis-Menten kinetics curve of each variant was created by using the DNA template-Cy5 in 8 concentrations of 2 nmol, 4 nmol, 5 nmol, 8 nmol, 10 nmol, 20 nmol, 40 nmol and 80 nmol. The temperature of the enzymatic reaction is 25° C.

The enzyme activity of the fusion protein of KOD DNA polymerase variant was measured according to the following kinetic detection mode, with data recorded once per minute.

| | |
|---|---|
| Extension wavelength | 530 nm |
| Emission wavelength | 676 nm |
| Reaction Temperature | 40° C. |
| Reaction time | 30 min |

After the enzymatic reaction was completed, data in a table form or the Michaelis-Menten kinetics curve can be directly obtained, based on which the reaction rate of relative fluorescence can be calculated.

Since the reaction rate of relative fluorescence depends on the concentration of the DNA template-Cy5, a Km value and Kcat/Km of the fusion protein of KOD DNA polymerase variant can be determined according to the enzymatic activity detected under different concentrations of the DNA template-Cy5, where the Km value refers to the concentration of DNA template-Cy5 corresponding to half of the maximum reaction rate of relative fluorescence.

The fusion protein of the wild-type KOD DNA polymerase (KOD-WT) was used as a control.

The KOD DNA polymerase variants Ue1E, Ue1E5 and Ue1E6 were used in this example, which were prepared as the method in Example 1.

The fusion proteins of the KOD DNA polymerase variants Ue1E, Ue1E5 and Ue1E6 are those which each connect with 6 His-tags at the C-terminus respectively compared to their corresponding KOD DNA polymerase variants Ue1E, Ue1E5 and Ue1E6.

Figure 2:
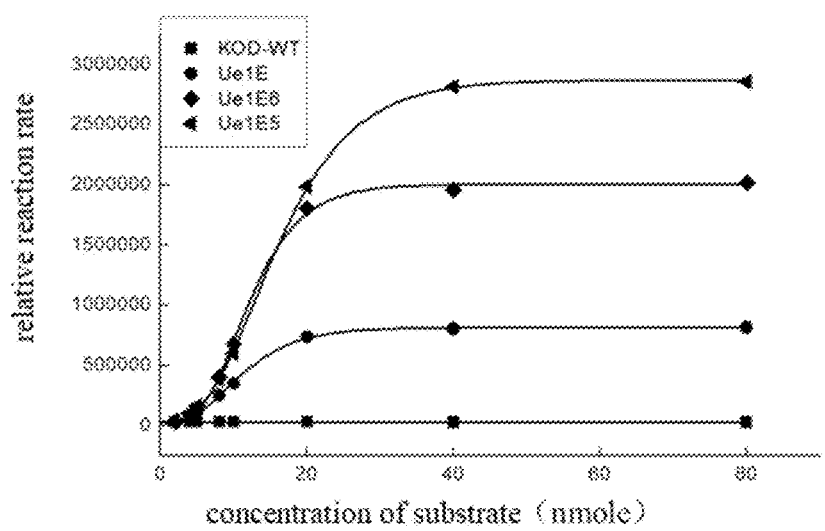
FIG. 2 is a schematic graph showing the Michaelis kinetics curves of the wild-type KOD DNA polymerase and its variants Ue1E, Ue1E5 and Ue1E6 in a substrate of a single-stranded DNA according to some embodiments of the present disclosure.

The Michaelis-Menten kinetics curves of variants Ue1E, Ue1E5 and Ue1E6 are shown in FIG. 2. The kinetics parameters of variants Ue1E, Ue1E5 and Ue1E6 are shown in Table 3 below.

TABLE 3

Kinetics parameters of variants Ue1E, Ue1E5 and Ue1E6

| Names | Km value (μM) | Kcat/km (min$^{-1}$M$^{-1}$) |
|---|---|---|
| Wild-type KOD DNA polymerase | None | None |
| Variant Ue1E | 13.2 | 20.4 |
| Variant Ue1E5 | 15.9 | 13.5 |
| Variant Ue1E6 | 14.6 | 17.9 |

It can be seen from FIG. 2 and Table 3, the KOD DNA polymerase variants Ue1E, Ue1E5 and Ue1E6 all exhibit better polymerization activity compared to the wild-type KOD polymerase (KOD-WT) when a single-stranded DNA was used as a template.

In addition, the results in this example indicate that a specific KOD DNA polymerase variant, whose Km value is approximate to the affinity of DNA polymerase and DNA template, remains its polymerization activity (i.e. catalytic reaction efficiency), thus being capable of realizing an ideal DNA binding affinity without affecting the specific catalytic properties. Therefore, the KOD DNA polymerase variants which have increased Km values can rapidly dissociate with DNA molecule, thus accelerating the polymerization reaction to some extent, and benefiting the elution of such the KOD DNA polymerase variant from a chip.

2.3 Activity Assay of Fusion Protein of KOD DNA Polymerase Variant on a Chip

The KOD DNA polymerase variant Ue1E5 described above was selected for detecting its activity on a chip, where the variant Ue1E5 has a mutation with isoleucine at position 408, a mutation with alanine at position 409, a mutation with glutamic acid at position 485, a mutation with methionine at position 53, a mutation with methionine at position 199, a mutation with methionine at position 243, a mutation with methionine at position 526, a mutation with alanine at position 674, and a mutation with methionine at position 709.

After the DNA template depicted in SEQ ID NO:7 synthesized by Genscript company was immobilized on a biochip gencbio amino substrate (Gencbio, GCB01003), the reaction between the fusion protein of KOD DNA polymerase variant Ue1E5 and the DNA template was conducted in a non-aqueous solution according to the following procedure.

After the amino-modified chip was washed with 0.2M phosphate buffer (0.2M NaH$_2$PO$_4$ and 0.2M Na$_2$HPO$_4$, PH7.0), 30 ng/μL DNA template in an appropriate amount was spread out over the whole chip and kept at room temperature for 15 minutes for immobilization, such that the DNA template with negative charges can be sufficiently immobilized on the surface of the chip with positive charges. After that, the chip was washed again with the enzyme reaction buffer in a pH 8.8 (including 20 mM Tris-HCl, 10 mM (NH$_4$)$_2$SO$_4$, 10 mM KCl and 2 mM MgSO$_4$) at 25° C. to remove the excess DNA template. Subsequently, a reaction system including 2U fusion protein of KOD DNA polymerase variant Ue1E5, 1 μM dATP-Cy3, 10 μM dTTP, 10 μM dCTP and 10 μM dGTP, and the enzyme reaction buffer was added to spread out over the whole chip and incubated at 65° C. for 15 minutes, followed by washing the chip with the phosphate buffer (0.2M, PH7.0) twice to remove excess dNTPs which are unreacted. After completion, the chip was observed and photographed by a fluorescence microscope according to the detection conditions of the Cy3 fluorescent dye (530 nm of excitation wavelength and 568 nm of emission wavelength). The wild-type KOD polymerase as a control was assayed similarly.

If more and denser bright spots are present in the photo obtained, the reaction between the fusion protein of KOD DNA polymerase variant and the DNA template immobilized on the chip is more sufficient, and the KOD DNA polymerase variant is of a stronger polymerization activity.

Figure 3:
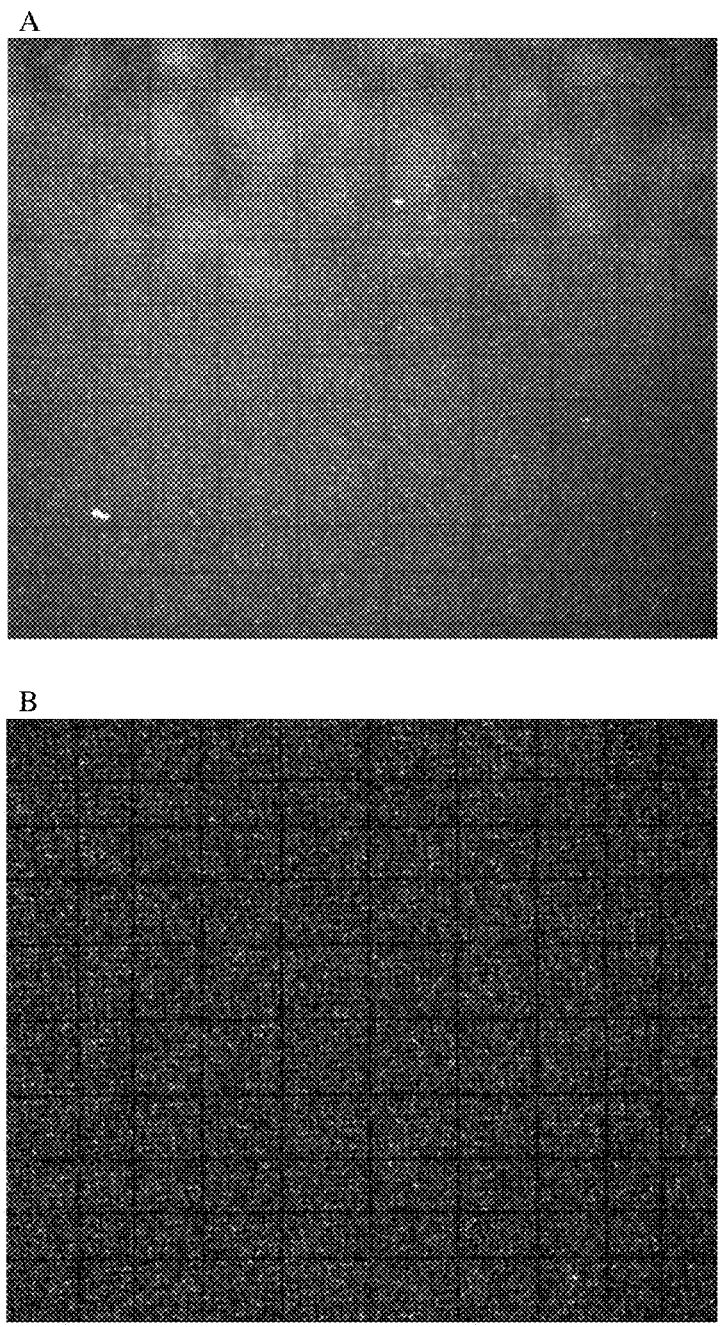
FIG. 3 is a schematic graph showing bright spots of the wild-type KOD DNA polymerase and its variant Ue1E5 present on a chip at an activity assay according to one embodiment of the present disclosure.

The results are shown in FIG. 3, where FIG. 3A indicates the result of the wild-type KOD polymerase and FIG. 3B indicates the result of KOD DNA polymerase variant Ue1E5. It can be seen, few bright spots are present on the chip in FIG. 3A, indicating the wild-type KOD polymerase which is unmodified or mutated exhibits a poor even no activity when reacting with the DNA template on the surface of the chip, while more and denser bright spots are present on the chip in FIG. 3B, which indicates the KOD DNA polymerase variant Ue1E5 is more active than the wild-type KOD polymerase when reacting with the DNA template on the surface of the chip.

The KOD DNA polymerase variants Ue1E and Ue1E6 were also tested for their activity on a chip as the method similar to Ue1E5, with results similar to Ue1E5, which indicates a good polymerization activity for the Ue1E and Ue1E6.

The fusion proteins of the KOD DNA polymerase variants are those which each connect with 6 His-tags at the C-terminus respectively compared to their corresponding KOD DNA polymerase variants.

2.4 Elution Assay of KOD DNA Polymerase Variant on a Chip

For an enzymatic reaction in a chip, the reaction residue in a previous step will interfere with a subsequent step, which can directly affect the photographing effect of the whole chip, thus it is ideal to remove the reaction residue left in the previous step during the enzymatic reaction.

In this example, KOD DNA polymerase variant Ue1E5 as an example was assayed for elution effect on a chip, while the commercial enzyme Therminator (Therminator™ DNA Polymerase, NEB, M0261S) was used as a control. The specific experimental methods are as follows.

The predetermined treatment of the chip and enzymatic reaction on the chip were conducted as the method described in 2.3.

After the photographing, the chip was washed 3 or 4 times with the enzyme reaction buffer in pH 8.8 including 20 mM Tris-HCl, 10 mM $(NH_4)_2SO_4$, 10 mM KCl and 2 mM $MgSO_4$ at 25° C., followed by incubating in a reaction system which contains dNTPs and the enzyme reaction buffer but without the DNA polymerase (i.e. the KOD DNA polymerase variant or the Therminator) at 65° C. for 15 minutes. After completion, the chip was washed with the enzyme reaction buffer twice, and further observed and photographed by the fluorescence microscope according to the detection conditions of the Cy3 fluorescent dye (530 nm of excitation wavelength and 568 nm of emission wavelength).

In this experiment, more bright spots present in a photo obtained means that the enzymatic reaction continues, which indicates the KOD DNA polymerase variant used still remains on the chip, suggesting such the variant is not easy to be eluted out.

Figure 4:
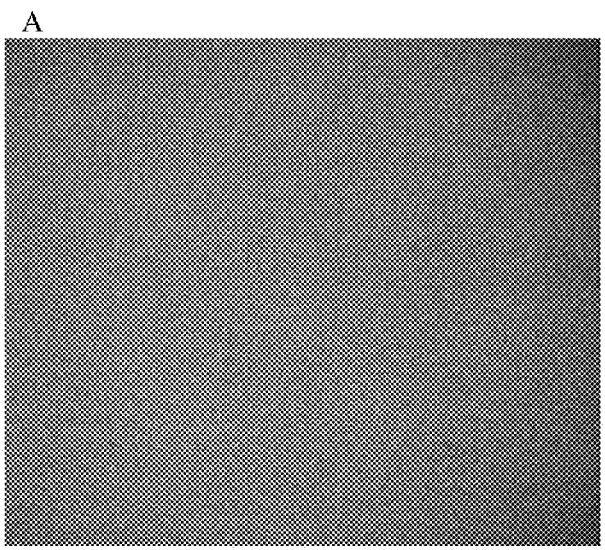
FIG. 4 is a schematic graph showing bright spots of the wild-type KOD DNA polymerase variant Ue1E5 and Terminator DNA polymerase as a control present on a chip at an elution assay according to one embodiment of the present disclosure.
Figure 4:
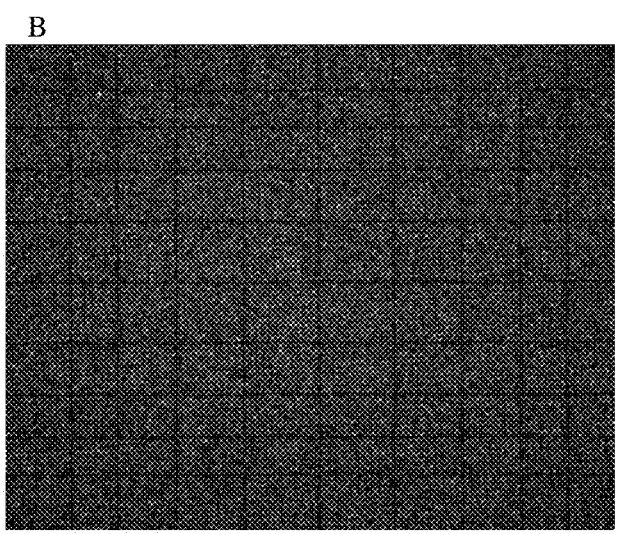
Figure 4:
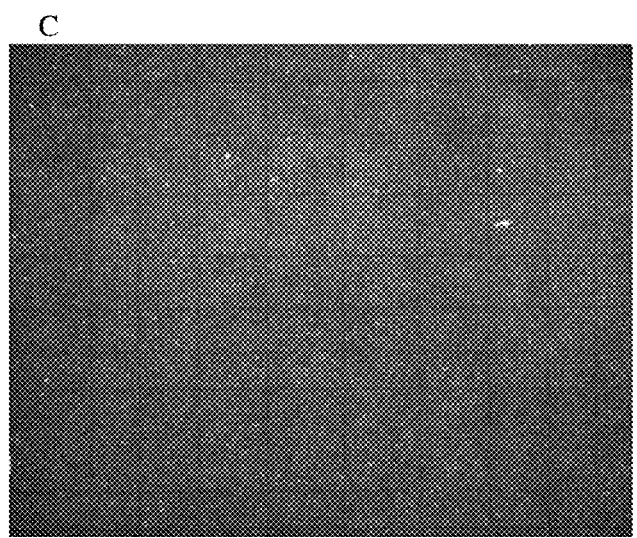

The experimental results are shown in FIG. 4, where FIG. 4A shows a blank control, i.e. a blank chip, FIG. 4B indicates the result of the Therminator, and FIG. 4C indicates the result of KOD DNA polymerase variant Ue1E5. It can be seen, no bright spots are present on the blank chip of FIG. 4A due to no enzymatic reaction, more bright spots are present in FIG. 4B compared to the blank control, and few bright spots are present in FIG. 4C which are more than those in the blank control and less than those shown in FIG. 4B, which indicates the KOD DNA polymerase variant Ue1E5 achieves a better elution effect than the Therminator, suggesting such the variant is easy to be eluted out, and is poor at adsorbing on the surface of the chip, thus without interference to subsequent steps.

The wild-type KOD DNA polymerase cannot be used for elution assay due to its poor polymerization activity, thus the commercial enzyme Therminator was used as a control.

The fusion protein of KOD DNA polymerase variant Ue1E was assayed according to the similar method, with a result similar to Ue1E5, showing Ue1E is easier to be eluted out than Therminator.

The fusion protein of KOD DNA polymerase variant Ue1E6 was assayed according to the similar method, with a result similar to Ue1E5, showing Ue1E6 is easier to be eluted out than Therminator.

Other KOD DNA polymerase variants (such as Ue1A, Ue1B, Ue1C, Ue1D, Ue2A, Ue2B, Ue2C, Ue2D, Ue2E, Ue3A, Ue3B, Ue3C, Ue3D, Ue3E, Ue4A, Ue4B, Ue4C, Ue1A5, Ue1A6, Ue1B5, Ue1B6, Ue1C5, Ue1C6, Ue1D5, Ue1D6, Ue2A5, Ue2A6, Ue2B5, Ue2B6, Ue2C5, Ue2C6, Ue2D5, Ue2D6, Ue2E5, Ue2E6, Ue3A5, Ue3A6, Ue3B5, Ue3B6, Ue3C5, Ue3C6, Ue3D5, Ue3D6, Ue3E5, Ue3E6, Ue4A5, Ue4A6, Ue4B5, Ue4B6, Ue4C5 and Ue4C6) were detected according to the similar method, and the results show all of them are easy to be eluted out and are poor at adsorbing on the surface of the chip.

2.5 Polymerization Efficiency Assay of KOD DNA Polymerase Variant on Sequencing Platform Wild-type KOD DNA polymerase could not be used for sequencing a specific DNA sequence to be sequenced on a sequencing platform because it cannot add an artificially modified nucleotide (i.e. non-natural) which is important for sequencing into the DNA sequence to be sequenced.

In this experiment, KOD DNA polymerase variant Ue1E as an example was assayed on a sequencing platform for its polymerization efficiency of sequencing. Such the sequencing procedure was conducted on BGI's Next generation sequencing platform through DNA nano ball (DNB)-sequencing method.

Specifically, the BGI's Next generation sequencing platform is BGISEQ-1000 (Black Bird) platform/BGISEQ-500 (Zebra) platform, with the sequencing parameters as below:

sequencer ID: 34;

sequencing read of 30 bp;

two chips including GS90004717-FS3 for Lane L01 and GS90004715-FS3 for Lane L02, in duplicate; and standard library type: AD153 E. coli.

The sequencing result obtained under the KOD DNA polymerase variant Ue1E was shown in Table 4 below.

TABLE 4

Sequencing result of KOD DNA polymerase variant Ue1E

| Sample ID | Lane | Lag | $R^2$ | RunOn | $R^2$ | Mapping Rate (%) |
|---|---|---|---|---|---|---|
| Ue1E | L01 | 0.28 | 0.98 | 0.07 | 0.97 | 83.1 |
| Ue1E | L02 | 0.31 | 0.97 | 0.07 | 0.96 | 82.4 |

It can be seen from Table 4 that the KOD DNA polymerase variant Ue1E can successfully perform sequencing on a sequencing platform under an artificially modified nucleotide with high accuracy and efficiency, thus the Ue1E has a good prospect in DNA sequencing on a specific sequencing platform.

Example 3: Activity Assay of Fusion Protein of C-Terminal Shortened KOD DNA Polymerase Variant on a Chip The fusion proteins of the KOD DNA polymerase variants are those which each connect with 6 His-tags at the C-terminus respectively compared to their corresponding KOD DNA polymerase variants.

The fusion proteins of C-terminal shortened KOD DNA polymerase variants prepared according to the method in 1.3 (including ΔUe1A, ΔUe1B, ΔUe1C, ΔUe1D, ΔUe1E, ΔUe2A, ΔUe2B, ΔUe2C, ΔUe2D, ΔUe2E, ΔUe3A, ΔUe3B, ΔUe3C, ΔUe3D, ΔUe3E, ΔUe4A, ΔUe4B and ΔUe4C) were respectively assayed for their polymerization activity as the method in 2.1 and their activity on a chip as the method in 2.3.

The fusion proteins of KOD DNA polymerase variants including Ue1A, Ue1B, Ue1C, Ue1D, Ue1E, Ue2A, Ue2B, Ue2C, Ue2D, Ue2E, Ue3A, Ue3B, Ue3C, Ue3D, Ue3E, Ue4A, Ue4B and Ue4C were respectively used as controls.

The results of the fusion proteins of C-terminal shortened KOD DNA polymerase variants (including Ue1A, ΔUe1B, ΔUe1C, ΔUe1D, ΔUe1E, ΔUe2A, ΔUe2B, ΔUe2C, ΔUe2D, ΔUe2E, ΔUe3A, ΔUe3B, ΔUe3C, ΔUe3D, ΔUe3E, ΔUe4A, ΔUe4B and ΔUe4C) are respectively similar to the results of corresponding fusion proteins of KOD DNA polymerase variants (including Ue1A, Ue1B, Ue1C, Ue1D, Ue1E, Ue2A, Ue2B, Ue2C, Ue2D, Ue2E, Ue3A, Ue3B, Ue3C, Ue3D, Ue3E, Ue4A, Ue4B and Ue4C).

The results demonstrated that deletion of amino acids 1 to 29 from the C-terminus of KOD DNA polymerase variant does not affect the activity of the variant.

The fusion proteins of C-terminal shortened KOD DNA polymerase variants in this example were respectively assayed according to the method in example 2.4, with the results showed that such the C-terminal shortened variants are not easy to be eluted out and are poor at adsorbing on the surface of the chip.

INDUSTRIAL APPLICATION

The examples of the present disclosure demonstrated that the DNA polymerase variants prepared in the present disclosure are capable of catalytically reacting with artificially modified nucleotides or their analogs as a substrate, with excellent polymerization activity, poor adsorption on the surface of a chip, and easily eluted from the surface of the chip, thereby allowing a single nucleotide or its analogs to be added in each reaction cycle, without interfering with the subsequent sequencing cycle due to its excellent elution property.

What is claimed is:

1. A DNA polymerase variant, comprising amino acid mutations at positions 408, 409 and 485 compared to the amino acid sequence of a wild-type KOD DNA polymerase depicted in SEQ ID NO:1, Wherein the amino acid mutation comprises:
substitution of leucine at position 408 with isoleucine, tyrosine, proline, valine, cysteine, serine, alanine or methionine;
substitution of tyrosine at position 409 with alanine or glycine; and
substitution of alanine at position 485 with histidine, asparagine, lysine, aspartic acid or glutamic acid,
wherein the DNA polymerase variant has DNA polymerase activity.

2. The DNA polymerase variant according to claim 1, wherein the DNA polymerase variant further comprises at least one of amino acid mutations at positions 53, 59, 199, 243, 526, 558, 613, 641, 671, 673, 674, 692 and 709 compared to the amino acid sequence of the wild-type KOD DNA polymerase.

3. The DNA polymerase variant according to claim 2, wherein the at least one of amino acid mutations at positions 53, 59, 199, 243, 526, 558, 613, 641, 671, 673, 674, 692 and 709 is selected from the group consisting of methionine, phenylalanine and Alanine.

4. The DNA polymerase variant according to claim 3, wherein the at least one of amino acid mutations at positions 53, 59, 199, 243, 526, 558, 613, 641, 671, 673, 674, 692 and 709 is selected from the group consisting of:
substitution of lysine at position 53 with methionine;
substitution of histidine at position 59 with phenylalanine;
substitution of lysine at position 199 with methionine;
substitution of arginine at position 243 with methionine;
substitution of lysine at position 526 with methionine;
substitution of lysine at position 558 with methionine;
substitution of arginine at position 613 with methionine;
substitution of arginine at position 641 with methionine;
substitution of lysine at position 671 with methionine;
substitution of tyrosine at position 673 with phenylalanine;
substitution of lysine at position 674 with alanine;
substitution of lysine at position 692 with methionine; and
substitution of arginine at position 709 with methionine.

5. The DNA polymerase variant according to claim 1, wherein the DNA polymerase variant is further modified by deleting amino acids 1 to 29 from the C-terminus of the DNA polymerase variant.

6. The DNA polymerase variant according to claim 1, wherein the DNA polymerase variant is further labeled at the N-terminus or C-terminus with a tag.

7. The DNA polymerase variant according to claim 5, wherein the DNA polymerase variant is further labeled at the N-terminus or C-terminus with a tag.

8. The DNA polymerase variant according to claim 6, wherein the tag is selected from Poly-Arg, Poly-His, FLAG, Strep-tag II and c-myc.

9. The DNA polymerase variant according to claim 7, wherein the tag is selected from Poly-Arg, Poly-His, FLAG, Strep-tag II and c-myc.

10. The DNA polymerase variant according to claim 1, wherein the DNA polymerase variant consists of the amino acid sequence of SEQ ID NO: 8, SEQ ID NO: 10 and SEQ ID NO: 12.

11. A nucleic acid encoding the DNA polymerase variant as defined in claim 1.

12. A method for sequencing, wherein the method is conducted under the DNA polymerase variant as defined in claim 1.

* * * * *

SEQUENCE LISTING

```
<160> NUMBER OF SEQ ID NOS: 13

<210> SEQ ID NO 1
<211> LENGTH: 774
<212> TYPE: PRT
<213> ORGANISM: Artificial Sequence
<220> FEATURE:
<223> OTHER INFORMATION: wild-type KOD DNA polymerase

<400> SEQUENCE: 1

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175
```

```
Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Gln Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590
```

```
Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 2
<211> LENGTH: 2322
<212> TYPE: DNA
<213> ORGANISM: Artificial Sequence
<220> FEATURE:
<223> OTHER INFORMATION: nucleotide sequence encoding wild-type KOD DNA
      polymerase

<400> SEQUENCE: 2
atgattctgg acaccgatta catcaccgaa gatggcaagc cagttatccg cattttcaaa      60
aaagagaatg gtgaattcaa gatcgaatat gatcgtacct tcgagccgta cttctatgct     120
ctgctgaaag acgatagcgc gattgaggag gtcaagaaaa tcaccgcgga gcgtcacggt     180
acggttgtta ccgtgaaacg cgtggagaaa gtccagaaga aatttctggg tcgcccggtt     240
gaagtgtgga agctgtactt tacgcatccg caagatgttc ggcgattcg cgataagatt     300 cgtgagcacc cggcagtcat tgacatctac gagtatgaca ttccgttcgc aagcgttat     360 ctgatcgata agggtctggt cccgatggag ggtgacgaag aactgaagat gctggcgttc     420
gacatcgaaa ctctgtacca cgagggtgaa gagtttgccg agggtccgat cttgatgatt     480
tcctacgcgg acgaagaggg cgcacgtgtt atcacgtgga aaatgttga tctgccgtat     540 gttgacgtcg taagcaccga gcgtgagatg atcaaacgtt ttctgcgcgt tgttaaagaa     600
aaagatcctg acgtgctgat cacctacaac ggtgacaatt tcgatttcgc gtacctgaag     660
aaacgttgcg aaaaactggg tattaacttc gcgctgggtc gcgatggctc tgaaccgaag     720
atccagcgca tgggtgatcg ttttgcggtc gaggtgaagg gtcgcattca tttcgacctg     780
tacccggtga ttcgtcgtac catcaacttg ccgacttaca ccctggaagc cgtctatgaa     840
gctgtatttg gtcaaccgaa agaaaaagtg tacgctgagg aaattacgac ggcgtgggaa     900
accggtgaga acctggagcg cgttgcacgt tattctatgg aggacgcgaa agttacctac     960
```

```
gaactgggta aagagttcct gccgatggag gcccaactgt cccgtctgat cggccaaagc    1020
ctgtgggacg ttagccgcag cagcaccggt aacttagttg aatggttctt gctgcgtaag    1080
gcatacgaac gcaatgagct ggcgccgaac aaaccggacg agaaagaatt ggcgcgtcgc    1140
cgccagagct atgagggtgg ttatgtcaaa gaaccggagc gcggcttgtg ggagaacatc    1200
gtctatttgg attttcgtag cctgtatccg agcatcatta tcacgcataa tgtgagcccg    1260
gatacgttga atcgtgaggg ctgtaaggaa tacgacgtgg cgcctcaggt tggccaccgt    1320
ttctgcaagg actttccggg ctttatcccg agcctgctgg gtgatttgct ggaggaacgt    1380
cagaaaatca agaagaagat gaaagcaacc attgatccga tcgagcgcaa attactggac    1440
taccgtcaac gtgcaatcaa gatcctggcg aattcgtatt atggttacta tggctacgcg    1500
cgtgcgcgct ggtattgcaa agagtgtgcc gagagcgtga ccgcttgggg tcgtgagtac    1560
attaccatga cgatcaaaga gattgaagag aaatacggct ttaaggttat ctatagcgac    1620
accgacggtt tctttgcaac tatccctggc gcagacgcag aaaccgttaa gaaaaaggca    1680
atggagtttc tgaagtatat caacgcgaag ttgccaggcg ccctggaact ggagtacgag    1740
ggcttctaca agcgtggctt tttcgtgacg aaaaagaaat acgctgttat tgatgaagag    1800
ggcaagatca cgacccgtgg cctgaaaatt gtgcgccgtg attggagcga aattgcaaaa    1860
gaaacgcaag cgcgtgtgct ggaagcgctg ctgaaggacg cgacgtcga aaaagctgtg     1920 cgtattgtta agaggtcac cgagaagctg agcaaatacg aggtcccgcc agagaaattg     1980
gtgattcacg aacagattac gcgtgacctg aaagactata aggccaccgg tccgcatgtc    2040
gcagtggcga agcgcctggc ggctcgcggt gtgaagatcc gtccgggtac cgtcattagc    2100
tatatcgtgc tgaagggcag cggtcgtatc ggcgaccgtg cgattccgtt cgacgaattt    2160
gatccgacca aacacaaata tgatgcggaa tactatattg agaaccaagt gctgccagcc    2220
gttgagcgta ttctgcgcgc cttcggttac gcaaggaag atctgcgtta ccagaaaact     2280
cgtcaggtcg gtctgtccgc atggctgaaa ccgaagggca cc                      2322

<210> SEQ ID NO 3
<211> LENGTH: 21
<212> TYPE: DNA
<213> ORGANISM: Artificial Sequence
<220> FEATURE:
<223> OTHER INFORMATION: Primer SQF

<400> SEQUENCE: 3
aattccacaa cggtttccct c                                               21

<210> SEQ ID NO 4
<211> LENGTH: 23
<212> TYPE: DNA
<213> ORGANISM: Artificial Sequence
<220> FEATURE:
<223> OTHER INFORMATION: Primer SQR

<400> SEQUENCE: 4
acctgaatat ggctcataac acc                                             23

<210> SEQ ID NO 5
<211> LENGTH: 18
<212> TYPE: DNA
<213> ORGANISM: Artificial Sequence
<220> FEATURE:
<223> OTHER INFORMATION: Primer S1A
```

-continued

<400> SEQUENCE: 5
aatgccgtaa caaccgct                                                       18

<210> SEQ ID NO 6
<211> LENGTH: 18
<212> TYPE: DNA
<213> ORGANISM: Artificial Sequence
<220> FEATURE:
<223> OTHER INFORMATION: Primer S2A

<400> SEQUENCE: 6
cgcggccttc ctagaagt                                                       18

<210> SEQ ID NO 7
<211> LENGTH: 309
<212> TYPE: DNA
<213> ORGANISM: Artificial Sequence
<220> FEATURE:
<223> OTHER INFORMATION: DNA template for DNA template-Cy5

<400> SEQUENCE: 7
gcgccgatct tccagtactc ggattacggc attgttggcg atgccgtgaa gatccttccg         60 cgctgaccg cagctttagc gcgttgatcc actctggcag gctgcatttt tggtcctgcc        120
gctgacaggg agctcttatg tccgaagata tctttgacgc catcatcgtc ggtgcagggc        180
ttgccggttc ggttgccgca ctggtgctcg cccgcgaagg ggcgcaagtg ttagttatcg        240
agcgtggcaa ttccgcaggt gccaagaacg tcaccggcgg cgtctctat gcccacagcc        300 tggaacaca                                                                309

<210> SEQ ID NO 8
<211> LENGTH: 774
<212> TYPE: PRT
<213> ORGANISM: Artificial Sequence
<220> FEATURE:
<223> OTHER INFORMATION: amino acid sequence of DNA polymerase variant
      Ue1E

<400> SEQUENCE: 8

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

```
Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Gly Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Ile Ala Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Glu Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575
```

```
Leu Glu Tyr Glu Gly Phe Tyr Lys Arg Gly Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 9
<211> LENGTH: 2322
<212> TYPE: DNA
<213> ORGANISM: Artificial Sequence
<220> FEATURE:
<223> OTHER INFORMATION: nucleotide sequence encoding DNA polymerase
      variant Ue1E

<400> SEQUENCE: 9
atgattctgg acaccgatta tcatcaccgaa gatggcaagc cagttatccg cattttcaaa      60
aaagagaatg gtgaattcaa gatcgaatat gatcgtacct tcgagccgta cttctatgct     120
ctgctgaaag acgatagcgc gattgaggag gtcaagaaaa tcaccgcgga gcgtcacggt     180
acggttgtta ccgtgaaacg cgtggagaaa gtccagaaga aatttctggg tcgcccggtt     240
gaagtgtgga agctgtactt tacgcatccg caagatgttc cggcgattcg cgataagatt     300
cgtgagcacc cggcagtcat tgacatctac gagtatgaca ttccgttcgc caagcgttat     360
ctgatcgata agggtctggt cccgatggag ggtgacgaag aactgaagat gctggcgttc     420
gacatcgaaa ctctgtacca cgagggtgaa gagtttgccg agggtccgat cttgatgatt     480
tcctacgcgg acgaagaggg cgcacgtgtt atcacgtgga aaaatgttga ctgccgtat      540 gttgacgtcg taagcaccga gcgtgagatg atcaaacgtt ttctgcgcgt tgttaaagaa     600
aaagatcctg acgtgctgat cacctacaac ggtgacaatt tcgatttcgc gtacctgaag     660
aaacgttgcg aaaaactggg tattaacttc gcgctgggtc gcgatggctc tgaaccgaag     720
atccagcgca tgggtgatcg ttttgcggtc gaggtgaagg tcgcattca tttcgacctg     780 tacccggtga ttcgtcgtac catcaacttg ccgacttaca ccctggaagc cgtctatgaa     840
gctgtatttg gtcaaccgaa agaaaaagtg tacgctgagg aaattacgac ggcgtgggaa     900
```

-continued

```
accggtgaga acctggagcg cgttgcacgt tattctatgg aggacgcgaa agttacctac    960
gaactgggta agagttcct gccgatggag gcccaactgt cccgtctgat cggccaaagc   1020
ctgtgggacg ttagccgcag cagcaccggt aacttagttg aatggttctt gctgcgtaag   1080
gcatacgaac gcaatgagct ggcgccgaac aaaccggacg agaaagaatt ggcgcgtcgc   1140
cgccagagct atgagggtgg ttatgtcaaa gaaccggagc gcggcttgtg ggagaacatc   1200
gtctatttgg attttcgtag cattgcaccg agcatcatta tcacgcataa tgtgagcccg   1260
gatacgttga atcgtgaggg ctgtaaggaa tacgacgtgg cgcctcaggt tggccaccgt   1320
ttctgcaagg acttt ccggg ctttatcccg agcctgctgg gtgatttgct ggaggaacgt   1380
cagaaaatca agaagaagat gaaagcaacc attgatccga tcgagcgcaa attactggac   1440
taccgtcaac gtgaaatcaa gatcctggcg aattcgtatt atggttacta tggctacgcg   1500
cgtgcgcgct ggtattgcaa agagtgtgcc gagagcgtga ccgcttgggg tcgtgagtac   1560
attaccatga cgatcaaaga gattgaagag aaatacggct ttaaggttat ctatagcgac   1620
accgacggtt tctttgcaac tatccctggc gcagacgcag aaaccgttaa gaaaaaggca   1680
atggagtttc tgaagtatat caacgcgaag ttgccaggcg ccctggaact ggagtacgag   1740
ggcttctaca agcgtggctt tttcgtgacg aaaaagaaat acgctgttat tgatgaagag   1800
ggcaagatca cgacccgtgg cctggaaatt gtgcgccgtg attggagcga aattgcaaaa   1860
gaaacgcaag cgcgtgtgct ggaagcgctg ctgaaggacg cgacgtcga aaaagctgtg   1920 cgtattgtta agaggtcac cgagaagctg agcaaatacg aggtcccgcc agagaaattg   1980
gtgattcacg aacagattac gcgtgacctg aaagactata aggccaccgg tccgcatgtc   2040
gcagtggcga agcgcctggc ggctcgcggt gtgaagatcc gtccgggtac cgtcattagc   2100
tatatcgtgc tgaagggcag cggtcgtatc ggcgaccgtg cgattccgtt cgacgaattt   2160
gatccgacca aacacaaata tgatgcggaa tactatattg agaaccaagt gctgccagcc   2220
gttgagcgta ttctgcgcgc cttcggttac cgcaaggaag atctgcgtta ccagaaaact   2280
cgtcaggtcg gtctgtccgc atggctgaaa ccgaagggca cc                     2322
```

<210> SEQ ID NO 10
<211> LENGTH: 774
<212> TYPE: PRT
<213> ORGANISM: Artificial Sequence
<220> FEATURE:
<223> OTHER INFORMATION: amino acid sequence of DNA polymerase variant Ue1E5

<400> SEQUENCE: 10

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Met Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110
```

-continued

```
Asp Ile Pro Phe Ala Lys Arg Tyr Leu Ile Asp Lys Gly Leu Val Pro
            115                 120                 125
Met Glu Gly Asp Glu Glu Leu Lys Met Leu Ala Phe Asp Ile Glu Thr
        130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Met Glu Lys Asp Pro Asp Val Leu Ile Thr
        195                 200                 205
Tyr Asn Gly Asp Asn Phe Asp Phe Ala Tyr Leu Lys Lys Arg Cys Glu
210                 215                 220
Lys Leu Gly Ile Asn Phe Ala Leu Gly Arg Asp Gly Ser Glu Pro Lys
225                 230                 235                 240
Ile Gln Met Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
    290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Gln Ser Tyr
    370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Ile Ala Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Glu Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Met Glu Ile
        515                 520                 525
```

Glu Glu Lys Tyr Gly Phe Lys Val Ile Tyr Ser Asp Thr Asp Gly Phe
        530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Ala Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Met Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 11
<211> LENGTH: 2322
<212> TYPE: DNA
<213> ORGANISM: Artificial Sequence
<220> FEATURE:
<223> OTHER INFORMATION: nucleotide sequence encoding DNA polymerase
      variant Ue1E5

<400> SEQUENCE: 11

```
atgattctgg acaccgatta catcaccgaa gatggcaagc cagttatccg cattttcaaa      60
aaagagaatg gtgaattcaa gatcgaatat gatcgtacct tcgagccgta cttctatgct     120
ctgctgaaag acgatagcgc gattgaggag gtcaagatga tcaccgcgga gcgtcacggt     180
acggttgtta ccgtgaaacg cgtggagaaa gtccagaaga aatttctggg tcgcccggtt     240
gaagtgtgga agctgtactt tacgcatccg caagatgttc ggcgattcg cgataagatt     300 cgtgagcacc cggcagtcat tgacatctac gagtatgaca ttccgttcgc caagcgttat     360
ctgatcgata agggtctggt cccgatggag ggtgacgaag aactgaagat gctggcgttc     420
gacatcgaaa ctctgtacca cgagggtgaa gagtttgccg agggtccgat cttgatgatt     480
tcctacgcgg acgaagaggg cgcacgtgtt atcacgtgga aaatgttga ctgccgtat      540 gttgacgtcg taagcaccga gcgtgagatg atcaaacgtt ttctgcgcgt tgttatggaa     600
```

```
aaagatcctg acgtgctgat cacctacaac ggtgacaatt tcgatttcgc gtacctgaag    660
aaacgttgcg aaaaactggg tattaacttc gcgctgggtc gcgatggctc tgaaccgaag    720
atccagatga tgggtgatcg ttttgcggtc gaggtgaagg gtcgcattca tttcgacctg    780
tacccggtga ttcgtcgtac catcaacttg ccgacttaca ccctggaagc cgtctatgaa    840
gctgtatttg gtcaaccgaa agaaaaagtg tacgctgagg aaattacgac ggcgtgggaa    900
accggtgaga acctggagcg cgttgcacgt tattctatgg aggacgcgaa agttacctac    960
gaactgggta agagttcct gccgatggag gcccaactgt cccgtctgat cggccaaagc   1020
ctgtgggacg ttagccgcag cagcaccggt aacttagttg aatggttctt gctgcgtaag   1080
gcatacgaac gcaatgagct ggcgccgaac aaaccggacg agaagaatt ggcgcgtcgc   1140 cgccagagct atgagggtgg ttatgtcaaa gaaccggagc gcggcttgtg ggagaacatc   1200
gtctatttgg attttcgtag cattgcaccg agcatcatta tcacgcataa tgtgagcccg   1260
gatacgttga tcgtgaggg ctgtaaggaa tacgacgtgg cgcctcaggt tggccaccgt   1320
ttctgcaagg actttccggg ctttatcccg agcctgctgg gtgatttgct ggaggaacgt   1380
cagaaaatca gaagaagat gaaagcaacc attgatccga tcgagcgcaa attactggac   1440
taccgtcaac gtgaaatcaa gatcctggcg aattcgtatt atggttacta tggctacgcg   1500
cgtgcgcgct ggtattgcaa agagtgtgcc gagagcgtga ccgcttgggg tcgtgagtac   1560
attaccatga cgatcatgga gattgaagag aaatacggct ttaaggttat ctatagcgac   1620
accgacggtt tctttgcaac tatccctggc gcagacgcag aaaccgttaa gaaaaaggca   1680
atggagtttc tgaagtatat caacgcgaag ttgccaggcg ccctggaact ggagtacgag   1740
ggcttctaca gcgtggctt tttcgtgacg aaaaagaaat acgctgttat tgatgaagag   1800
ggcaagatca cgacccgtgg cctggaaatt gtgcgccgtg attggagcga aattgcaaaa   1860
gaaacgcaag cgcgtgtgct ggaagcgctg ctgaaggacg cgacgtcga aaagctgtg   1920 cgtattgtta agaggtcac cgagaagctg agcaaatacg aggtcccgcc agagaaattg   1980
gtgattcacg aacagattac gcgtgacctg aaagactata tggccaccgg tccgcatgtc   2040
gcagtggcga agcgcctggc ggctcgcggt gtgaagatcc gtccgggtac cgtcattagc   2100
tatatcgtgc tgaagggcag cggtgtgatc ggcgaccgtg cgattccgtt cgacgaattt   2160
gatccgacca acacaaaata tgatgcggaa tactatattg agaaccaagt gctgccagcc   2220
gttgagcgta ttctgcgcgc cttcggttac cgcaaggaag atctgcgtta ccagaaaact   2280
cgtcaggtcg gtctgtccgc atggctgaaa ccgaagggca cc                       2322
```

<210> SEQ ID NO 12
<211> LENGTH: 774
<212> TYPE: PRT
<213> ORGANISM: Artificial Sequence
<220> FEATURE:
<223> OTHER INFORMATION: amino acid sequence of DNA polymerase variant Ue1E6

<400> SEQUENCE: 12

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

```
Glu Glu Val Lys Lys Ile Thr Ala Glu Arg Phe Gly Thr Val Thr
    50              55                  60

Val Lys Arg Val Glu Lys Val Gln Lys Phe Leu Gly Arg Pro Val
65              70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Ile Ala Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460
```

```
Lys Lys Met Lys Ala Thr Ile Asp Pro Ile Glu Arg Lys Leu Leu Asp
465                 470                 475                 480

Tyr Arg Gln Arg Glu Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Met Lys Ala
545                 550                 555                 560

Met Glu Phe Leu Lys Tyr Ile Asn Ala Lys Leu Pro Gly Ala Leu Glu
            565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Met Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Met Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Met Asp
            660                 665                 670

Phe Lys Ala Thr Gly Pro His Val Ala Val Ala Lys Arg Leu Ala Ala
            675                 680                 685

Arg Gly Val Met Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770
```

<210> SEQ ID NO 13
<211> LENGTH: 2322
<212> TYPE: DNA
<213> ORGANISM: Artificial Sequence
<220> FEATURE:
<223> OTHER INFORMATION: nucleotide sequence encoding DNA polymerase
      variant Ue1E6

<400> SEQUENCE: 13

```
atgattctgg acaccgatta catcaccgaa gatggcaagc cagttatccg catttttcaaa    60 aaagagaatg gtgaattcaa gatcgaatat gatcgtacct tcgagccgta cttctatgct   120
```

-continued

```
ctgctgaaag acgatagcgc gattgaggag gtcaagaaaa tcaccgcgga gcgtttcggt      180
acggttgtta ccgtgaaacg cgtggagaaa gtccagaaga aatttctggg tcgcccggtt      240
gaagtgtgga agctgtactt tacgcatccg caagatgttc cggcgattcg cgataagatt      300
cgtgagcacc cggcagtcat tgacatctac gagtatgaca ttccgttcgc caagcgttat      360
ctgatcgata agggtctggt cccgatggag ggtgacgaag aactgaagat gctggcgttc      420
gacatcgaaa ctctgtacca cgagggtgaa gagtttgccg agggtccgat cttgatgatt      480
tcctacgcgg acgaagaggg cgcacgtgtt atcacgtgga aaaatgttga tctgccgtat      540
gttgacgtcg taagcaccga gcgtgagatg atcaaacgtt ttctgcgcgt tgttaaagaa      600
aaagatcctg acgtgctgat cacctacaac ggtgacaatt tcgatttcgc gtacctgaag      660
aaacgttgcg aaaaactggg tattaacttc gcgctgggtc gcgatggctc tgaaccgaag      720
atccagcgca tgggtgatcg ttttgcggtc gaggtgaagg gtcgcattca tttcgacctg      780
tacccggtga ttcgtcgtac catcaacttg ccgacttaca ccctggaagc cgtctatgaa      840
gctgtatttg gtcaaccgaa agaaaaagtg tacgctgagg aaattacgac ggcgtgggaa      900
accggtgaga acctggagcg cgttgcacgt tattctatgg aggacgcgaa agttacctac      960
gaactgggta agagttcct gccgatggag gcccaactgt cccgtctgat cggccaaagc     1020
ctgtgggacg ttagccgcag cagcaccggt aacttagttg aatggttctt gctgcgtaag     1080
gcatacgaac gcaatgagct ggcgccgaac aaaccggacg agaagaatt ggcgcgtcgc     1140 cgccagagct atgagggtgg ttatgtcaaa gaaccggagc gcggcttgtg ggagaacatc     1200
gtctatttgg attttcgtag cattgcaccg agcatcatta tcacgcataa tgtgagcccg     1260
gatacgttga tcgtgagggg ctgtaaggaa tacgacgtgg cgcctcaggt tggccaccgt     1320
ttctgcaagg actttccggg ctttatcccg agcctgctgg gtgatttgct ggaggaacgt     1380
cagaaaatca agaagaagat gaaagcaacc attgatccga tcgagcgcaa attactggac     1440
taccgtcaac gtgaaatcaa gatcctggcg aattcgtatt atggttacta tggctacgcg     1500
cgtgcgcgct ggtattgcaa agagtgtgcc gagagcgtga ccgcttgggg tcgtgagtac     1560
attaccatga cgatcaaaga gattgaagag aaatacggct ttaaggttat ctatagcgac     1620
accgacggtt tctttgcaac tatccctggc gcagacgcag aaaccgttaa gatgaaggca     1680
atggagtttc tgaagtatat caacgcgaag ttgccaggcg ccctggaact ggagtacgag     1740
ggcttctaca agcgtggctt tttcgtgacg aaaaagaaat acgctgttat tgatgaagag     1800
ggcaagatca cgaccgtgg cctggaaatt gtgcgcatgg attggagcga aattgcaaaa     1860
gaaacgcaag cgcgtgtgct ggaagcgctg ctgaaggacg gcgacgtcga aaaagctgtg     1920
atgattgtta agaggtcac cgagaagctg agcaaatacg aggtcccgcc agagaaattg     1980
gtgattcacg aacagattac gcgtgacctg atggacttta aggccaccgg tccgcatgtc     2040
gcagtggcga agcgcctggc ggctcgcggt gtgatgatcc gtccgggtac cgtcattagc     2100
tatatcgtgc tgaagggcag cggtcgtatc ggcgaccgtg cgattccgtt cgacgaattt     2160
gatccgacca acacacaaata tgatgcggaa tactatattg agaaccaagt gctgccagcc     2220
gttgagcgta ttctgcgcgc cttcggttac cgcaaggaag atctgcgtta ccagaaaact     2280
cgtcaggtcg gtctgtccgc atggctgaaa ccgaagggca cc                        2322
```